United States Patent

Liardet

[11] Patent Number: 6,035,896
[45] Date of Patent: Mar. 14, 2000

[54] VALVE

[75] Inventor: Claude Liardet, Aubonne, Switzerland

[73] Assignee: Varioraw Percutive S.A., Aubonne, Switzerland

[21] Appl. No.: 09/029,433

[22] PCT Filed: Aug. 29, 1996

[86] PCT No.: PCT/CH96/00298

§ 371 Date: Mar. 2, 1998

§ 102(e) Date: Mar. 2, 1998

[87] PCT Pub. No.: WO97/09552

PCT Pub. Date: Mar. 13, 1997

[30] Foreign Application Priority Data

Sep. 1, 1995 [CH] Switzerland ............... 2494/95

[51] Int. Cl.[7] .................................................. F16K 15/14
[52] U.S. Cl. ........................ 137/849; 137/512.4
[58] Field of Search ................... 137/512.4, 849, 137/843, 527, 527.8; 251/212

[56] References Cited

U.S. PATENT DOCUMENTS

| | | | |
|---|---|---|---|
| 3,113,586 | 12/1963 | Edmark, Jr. | 137/512.1 |
| 3,861,416 | 1/1975 | Wichterle | 137/525.3 |
| 4,053,084 | 10/1977 | Anderson | 137/849 |
| 4,308,885 | 1/1982 | Geisseler | 137/67 |
| 4,465,102 | 8/1984 | Rupp | 137/849 |
| 4,905,726 | 3/1990 | Kasugai et al. | 137/433 |

*Primary Examiner*—Denise L. Ferensic
*Assistant Examiner*—Joanne Y. Kim
*Attorney, Agent, or Firm*—Woodard, Emhardt, Naughton Moriarty & McNett, Patent and Trademark Attorneys

[57] ABSTRACT

The invention concerns a valve comprising a circular frame (1) whose inner edge narrows to form flexible areas (3) connecting the frame to triangular vanes (2). The areas (3) form articulations about which the vanes pivot when the valve opens or closes. In the closed position, the vanes bear against one another and the assembly adopts a pyramidal position. The valve can be produced by the injection of plastics. The entire valve may be produced in a single part.

13 Claims, 6 Drawing Sheets

VALVE

The invention concerns a valve capable of being used in flow tubes of different types. This valve features certain improved properties with regard, in particular, to its manner of opening, allowing for the maximum passage of the fluids.

There is a need for valves of this type in different sectors, particularly in the construction of medical equipment, for example in equipment for the care of the respiratory tract. In this sector, devices are known which have a therapeutic role, the aim of which is to improve the respiratory function of the patients (for example, EP-A0565489), while at the same time dispensing a medication in the form of droplets or particles in the flow of air which is inhaled. These devices comprise a number of different tubes connected to a mouthpiece, and which are fitted with valves to allow the patient to carry out alternating inhalation and exhalation.

In order for these devices to take effect properly, the valves intended for the conveying of the medication during inhalation must allow, in the open position, for the maximum cross-section of the passage for the flow of air, and for closure rapidly and completely as soon as the inhalation effort has ceased. In addition to this, the arrangement of the elements of the valve must be such that the flow is not disturbed, that in particular it remains laminar, and that the depositing of medication on the walls of the valve or the walls of the tube will be avoided.

It is noted that no existing valve satisfies these conditions in an entirely acceptable manner. In particular, tests conducted with the existing systems have demonstrated losses of active substance of up to 80%, which in the case of expensive medications, or medications difficult to apply in sufficient quantities on the target tissue, represent a considerable economic loss.

The valve according to the invention is a valve comprising a fitting in the form of a rigid frame and a shutoff element comprising an assembly of vanes connected to the frame by articulations, and pivoting about said articulations when opening under the effect of the introduction of the fluid.

Valves of this type are described in U.S. Pat. No. 4,351,358, and in the published version of the French patent application Nos 2 410 198 and 2 548 162.

The shutoff element described in the first of these documents comprises an open-work pyramidal fitting, the shutoff element being formed from a group of flat triangular vanes mounted on spring-loaded articulations, around the fitting. In the closed position, each plate is supported against one of the faces of the pyramid.

The two French documents describe shutoff devices formed from two vanes in the form of a segment of a cone or a segment of a cylinder, each connected to the seat by a spring-loaded articulation. In the closed position, each vane rests on the flat ring-shaped surface of the seat, and is in contact with the other vane.

The shutoff devices described in these three documents, of somewhat complicated design, are provided with external springs. They are intended for tubes for the passage of industrial fluids, but they are not suitable for equipment for providing care for the respiratory tract.

A valve intended for a respiration device is described in Belgian Patent No. 1005924. This comprises an element derived by cutting out from a single sheet of elastomer material, of constant thickness across its whole surface. This valve does not, properly speaking, constitute a non-return clack valve, but operates in both directions, with different resistance pressures. To this end, the sheet which is cut off forms a central disk connected by a tongue linkage to a ring element which surrounds it, the central area of the disk being divided into several sections by radial slots. The sheet is mounted in the wall of a tube, and a rigid seat is provided for, which serves to support the periphery of the disk. Accordingly, in one direction, the tongue bends, and the disk moves off the seat, like a normal clack valve, while in the other direction the periphery of the disk is supported against the seat, and the parts separated by the radial slots bend under the effect of the flow, in such a way that a certain yield can pass with a higher level of resistance than in the other direction. Such a valve does not allow for the conditions referred to above to be satisfied.

The aim of the present invention is therefore to create a valve which avoids the disadvantages referred to above, while still providing an economical and practical method of operation.

With this aim, the invention proposes a valve which comprises a fitting in the form of a rigid frame and a shutoff device, consisting of an assembly of vanes connected to the frame by a number of articulations and pivoting around these articulations during opening, under the effect of the introduction of the fluid, characterised in that the frame and the vanes form a single element, in which the vanes are rigid elements and the articulations of the flexible areas are each located between a vane and a corresponding portion of the frame, and in that the vanes are mutually shaped in such a way as to ensure the retention of the fluid in the closed position, by the support of the vanes against one another.

According to a first embodiment of the valve, the frame and the assembly of vanes are formed from the same piece, in a homogenous material, the articulations being thin areas of the said piece, each located between a vane and a corresponding portion of the frame, the said homogenous material being possibly a crystalline plastic material, particularly polyacetal.

According to a second embodiment of the valve, the articulations are created with the aid of an elastic material, and of an elastomer in particular.

The frame may be circular in shape or polygonal, or any other suitable shape, and may be formed from one piece with a segment of the tube guiding the flow, or incorporated in a segment of the tube guiding the flow.

The vanes may normally be triangular in shape, or the edges of the vanes may be curved inwards in such a way as to create a helicoidal thrust to the flow in the open position.

The segment of the tube may feature hollows, intended to accommodate the vanes in the open position.

The valve according to the invention can to advantage be used in medical equipment, and in respiratory equipment in particular.

Described hereinafter, by way of example, are various possible embodiments of the object of the invention, and different variants, making reference to the appended drawings, where:

Figure 8:
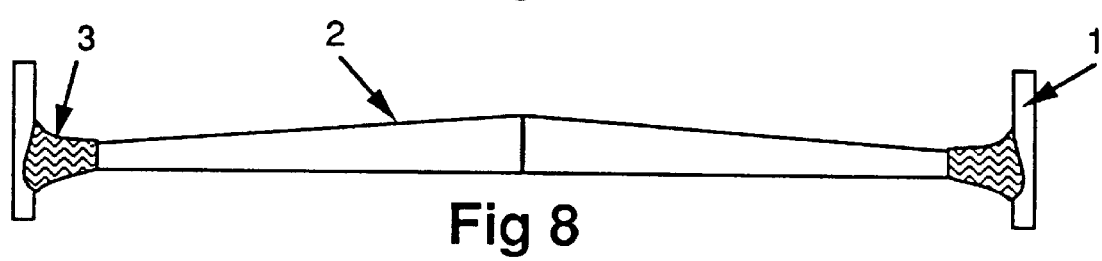

In general, the valves according to the embodiments of FIGS. 1 to 22, with the exception of the embodiment shown in FIG. 8, are designed in such a way that all their functional elements are established in the same piece, certain parts being elastically flexible, while the others are rigid. Materials are chosen for this which are suitable for these purposes, such as, for example, polyacetal, which can be highly flexible in its thin areas, and resistant in its thick areas. This material can be injection-moulded. In general, any hard plastic unbreakable material with characteristics resembling those of steel may be suitable. Certain crystalline plastics are known to feature such properties. In addition, steel itself may prove suitable in certain cases, although machining will in this case be lengthy and expensive in comparison with plastic injection moulding. It is likewise possible to achieve the characteristics described above by combining several materials, in particular as illustrated in FIG. 8, which features vanes made of a hard material, with the flexion area being made of an elastic material, such as, for example, an elastomer.

FIGS. 1 to 7 show how the embodiment in one piece can be achieved. The valve consists of a fixed and rigid part, in the form of a circular frame 1 of trapezoidal profile, from which extend parts 2 triangular in shape, which play the part of movable vanes. The vanes 2 are rigid, and connected to the frame 1 by thin areas 3, which ensure the articulation of the vanes about an axis which coincides with the base of the triangle. In the closed position, the vanes are supported against one another by their edge surfaces 4, and may form a low pyramid (which is the situation with the vanes of the valves in FIGS. 1 to 6), or can be positioned horizontally (which is the case with the vanes of the valves in FIGS. 7 and 8).

Figure 1:
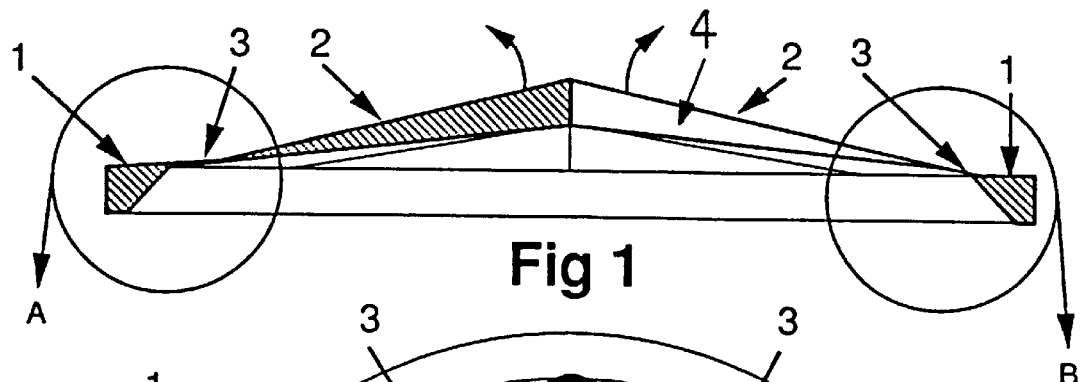
FIG. 1 is a sectional view along the line I—I of FIG. 2, showing a first embodiment of the valve.
Figure 2:
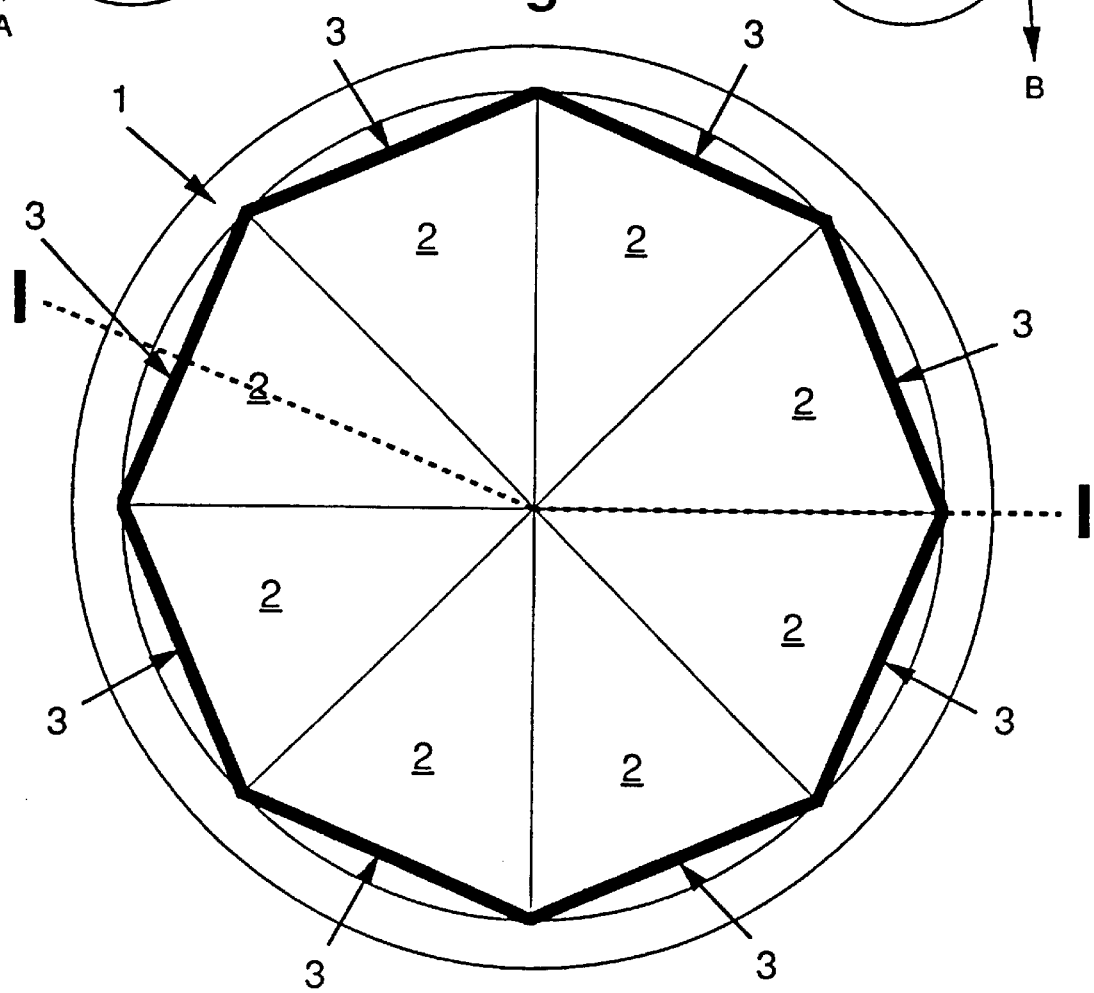
FIG. 2 is a plan view of this first embodiment.
Figure 3:
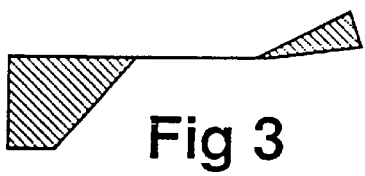
FIGS. 3 and 4 are enlargements respectively of the details A and B of FIG. 1.
Figure 4:
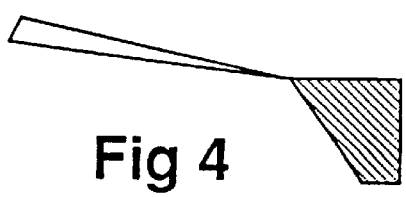

In the embodiment according to FIGS. 1 and 2, the longitudinal profile of the vanes 2 is triangular. Their thickness is maximum at the central point of juncture where all the vanes are in contact, and decreases steadily towards the periphery of the valve. The flexible areas 3 are, in plan, in the shape of disk segments.

Figure 5:
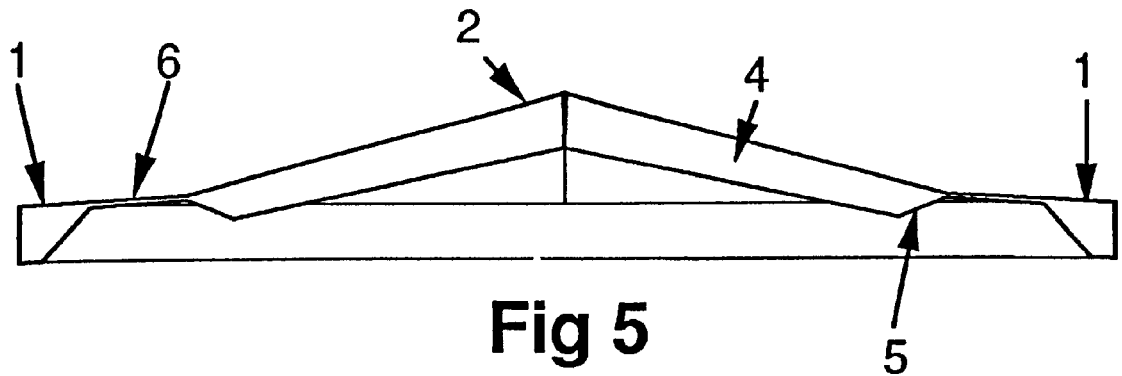
FIGS. 5 and 6 are views, respectively sectional through a diameter plane, and a plan view, of a second embodiment of the valve.
Figure 6:
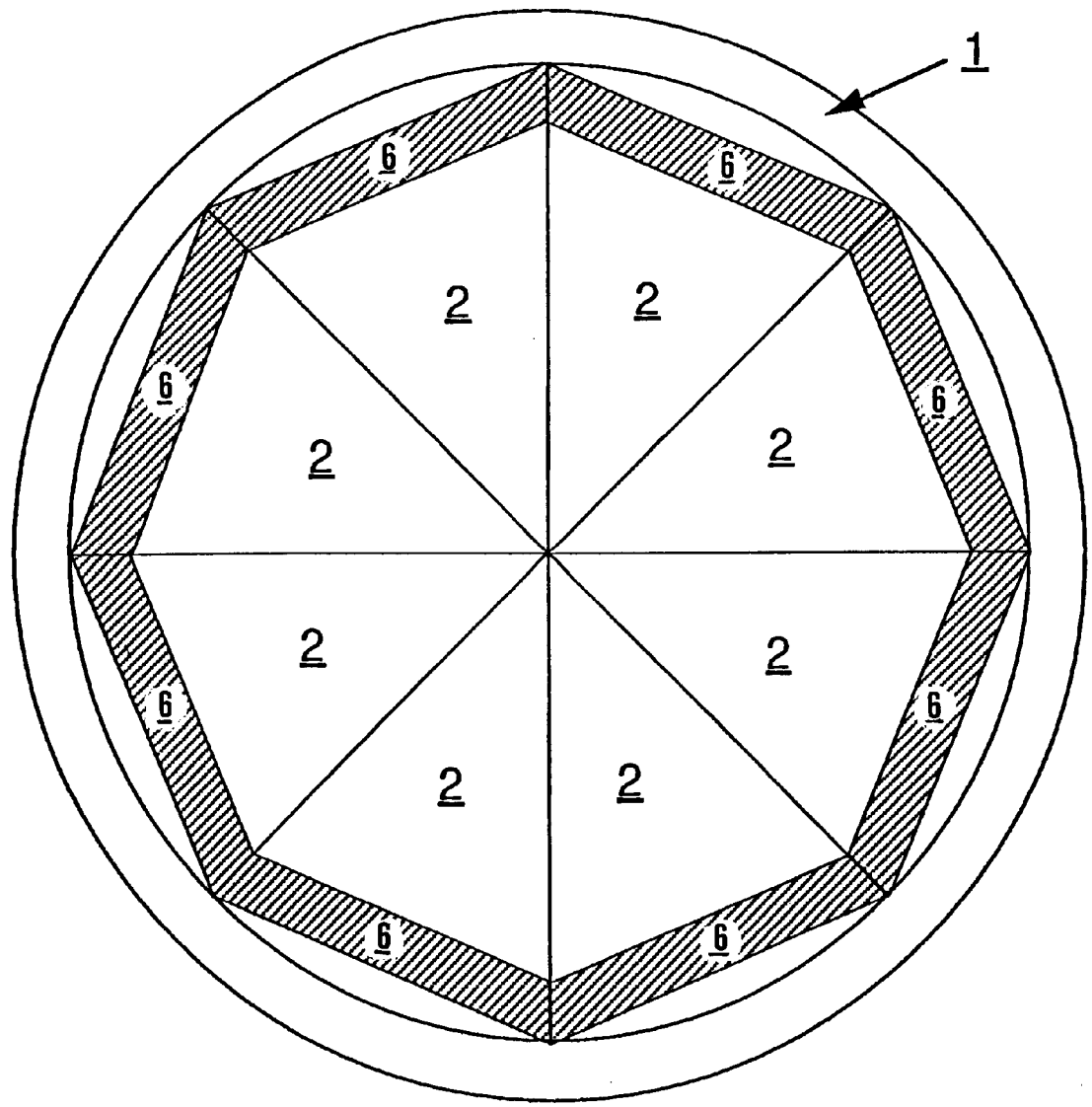
Figure 7:
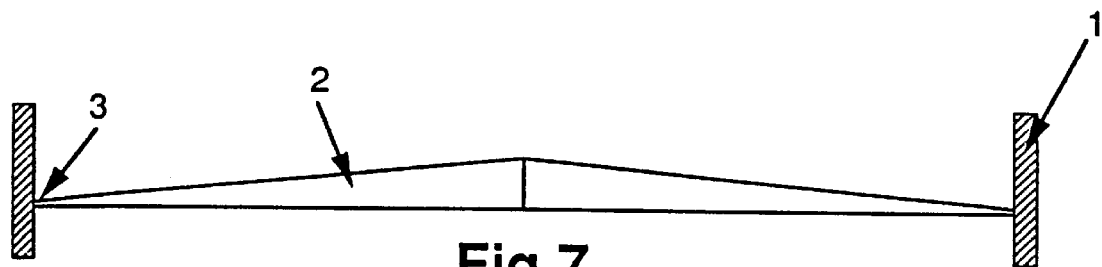
FIGS. 7 and 8 are sectional views through a diameter plane of two other embodiments of the valve.

In the embodiment according to FIGS. 5 and 6, the thickness of the vanes is constant from the common central point of support as far as the edge of the rigid area. Portions of the surface in conical segments 5 delimit the flexible areas 6, which are themselves arranged in accordance with the conical portions. These thin portions could also be connected to the vanes at the level of their lower surface.

Figure 9:
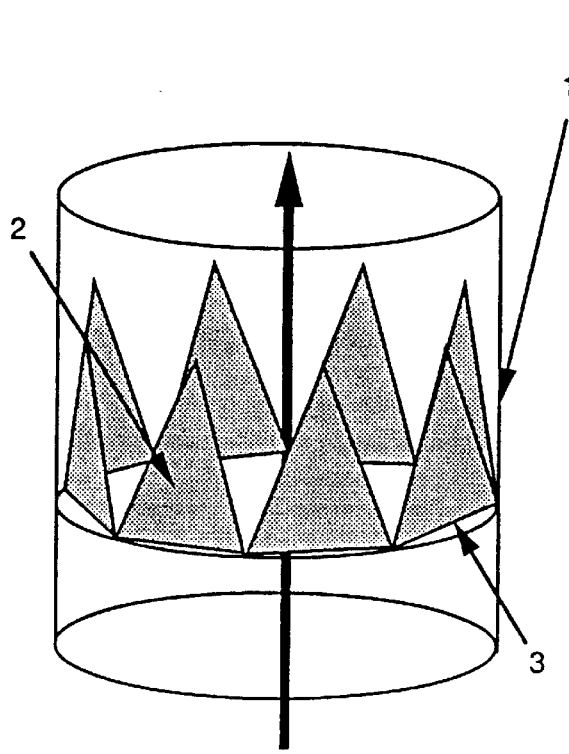
FIGS. 9 and 10 are schematic perspective views showing the valves of FIGS. 1 to 8 in the open and closed positions respectively.
Figure 10:
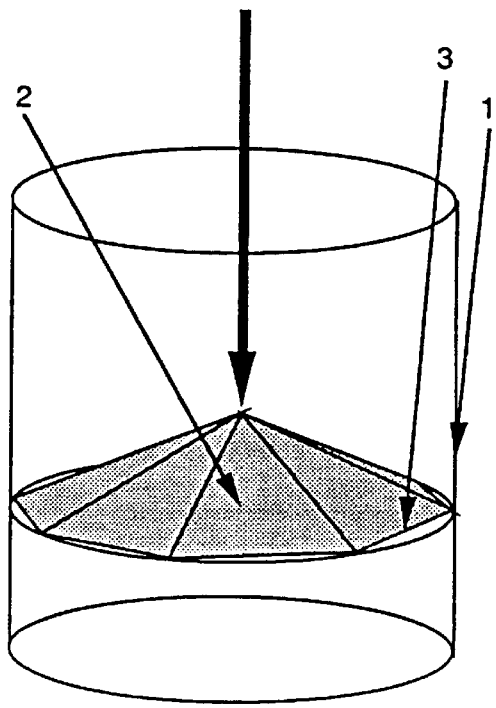
Figure 11:
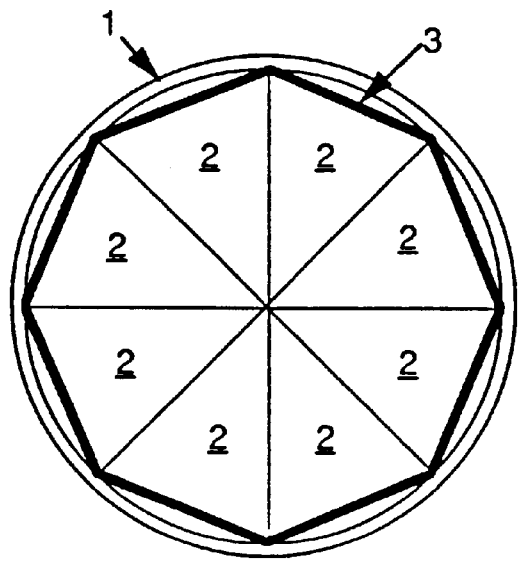
FIGS. 11 to 13 are schematic plan views showing different variations in respect of the number and shape of the vanes, for a circular tube.

The valves of the first two embodiments are intended to be fitted in a tube of circular profile by any suitable means: force engagement of the circle 1 in the inside face of the tube, locking against a shoulder projection by means of a spring-loaded ring, or fastening by means of a nut, etc. Under the effect of the pressure exerted by the mass of air introduced, the vanes pivot about their base, and are then located in the line of the tube, thus offering the minimum of resistance to the passage of the air. FIG. 9 shows in schematic form these positions, while the arrows of FIG. 1 indicate the direction of the pivoting movement. The valve closes (FIG. 10) under the effect of the elasticity of the areas 3, once the effect of the introduction of the air ceases.

Figure 12:
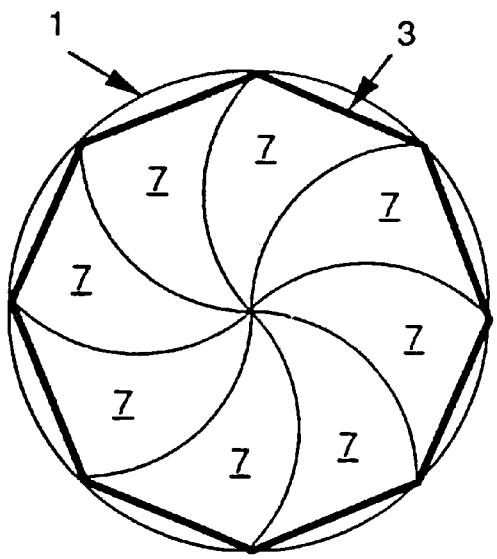
Figure 13:
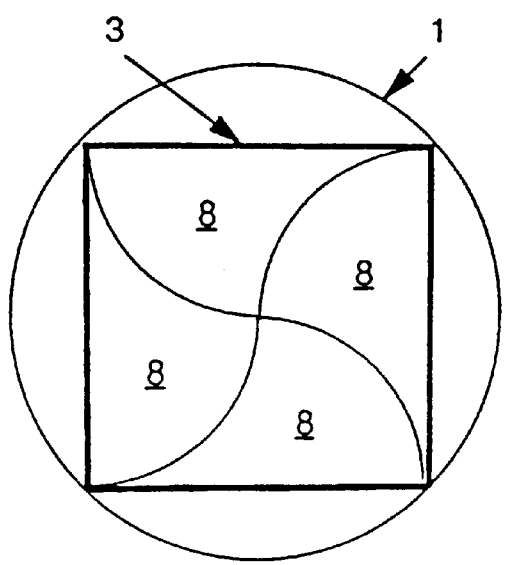
Figure 14:
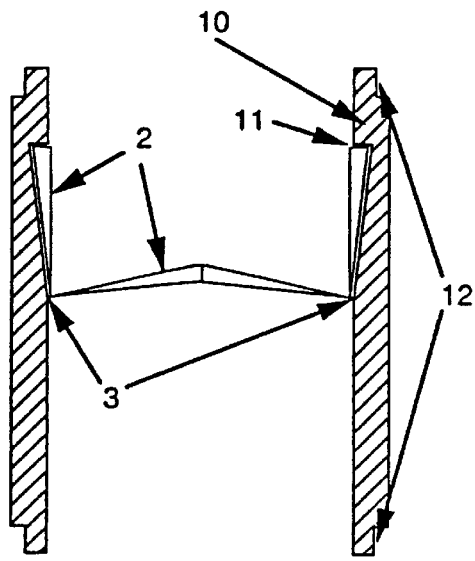
FIGS. 14 to 17 are schematic sectional views showing embodiments in which the valve proper is secured to a segment of the tube.
Figure 15:
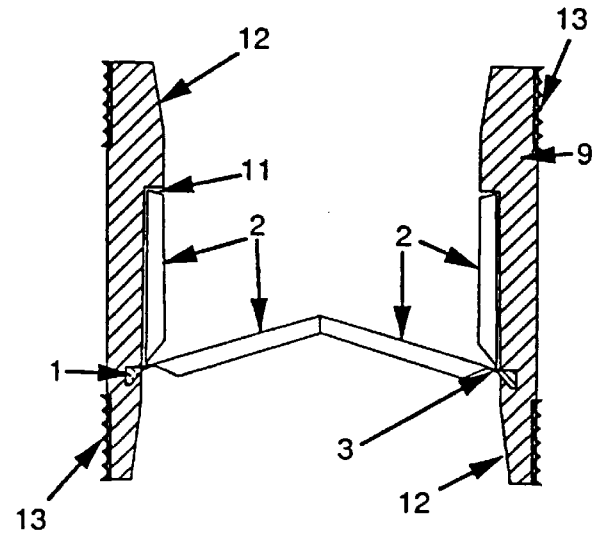
Figure 16:
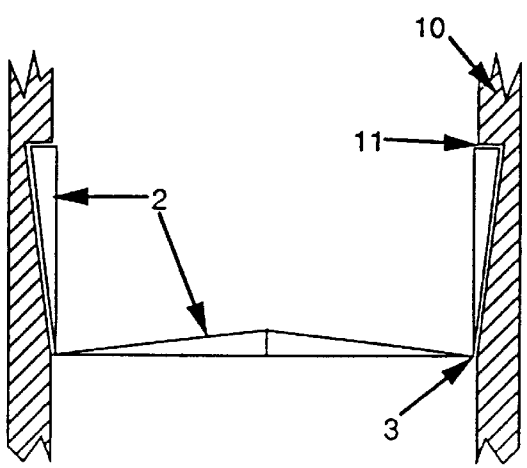
Figure 17:
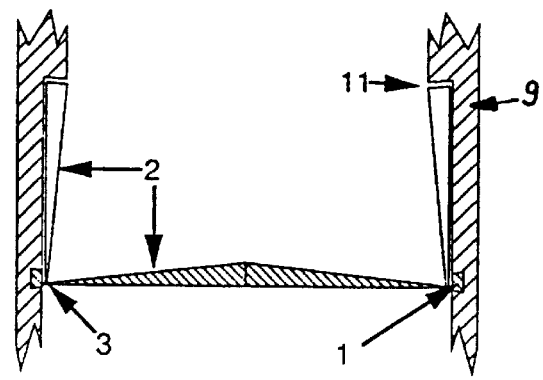
Figure 18:
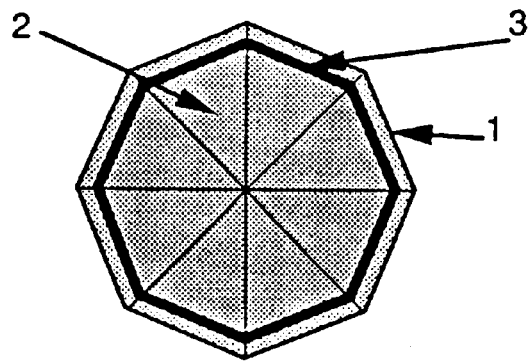
FIGS. 18 to 22 are schematic plan views showing different variations in relation to the section of the tube.
Figure 19:
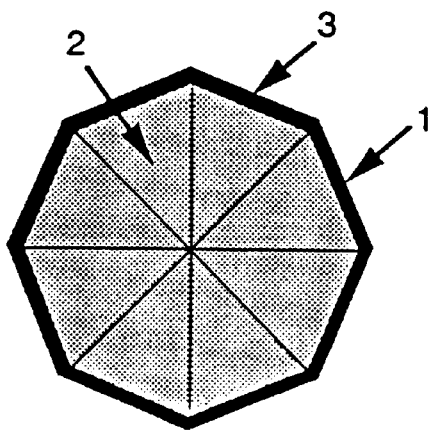
Figure 20:
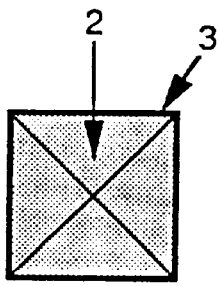
Figure 21:
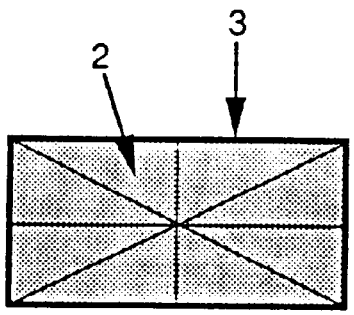
Figure 22:
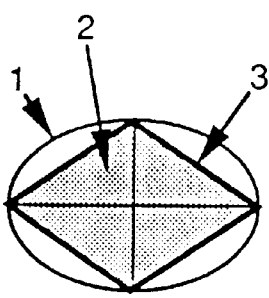

Instead of the vanes 2 being of triangular shape in their plan view, they may also, as shown in FIGS. 12 and 13, take the shape of curvilinear triangles 7 and 8. FIG. 12 shows an embodiment of eight vanes, as in FIGS. 1 to 4, and FIG. 13 represents a four-vane embodiment. The shape of the curvilinear triangle in FIGS. 12 and 13 features the advantage of providing the air flow with a rotation movement in a helical pattern around the axis of the tube. In this case, the recesses 11 in the thickness of the tube, intended to accommodate the vanes in the open position (described hereinafter with regard to FIGS. 14 to 17) will preferably not be provided. In this case it is in fact necessary that, in the open position, the ends of the vanes must be pointed towards the interior of the tube in order to convey the movement of rotation to the air flow.

In the event of the rigid frame of the valve not being circular in shape, but of polygonal form, octagonal for example (FIGS. 18 and 19), square (FIG. 20), or rectangular (FIG. 21), the thin areas 3 are straight rectilinear strips and no longer segments of disks. Valves with such polygonal frames, intended more particularly for tubes of correspondingly polygonal shapes, allow for better flow passage than is the case with circular profile tubes. It is of course possible to create valves with frames other than these, such as, for example, ellipses (FIG. 22), although, in this case, the air flow is less satisfactory.

Finally, FIGS. 14 to 17 show embodiments in which a segment of the tube 9 or 10 is linked to the valve proper. According to FIGS. 15 and 17, the rigid frame of the valve is embedded in the thickness of this segment of the tube 9, which may be of a different material to the valve, while according to FIGS. 14 and 16 it is the segment of the tube 10 itself which forms the rigid frame of the valve. In the four examples, cutouts 11 are provided for in the thickness of the tube to accommodate the the vanes in the open position, so that they offer the minimum of resistance to the passage of the air, and avoid the retention of droplets of medication incorporated in the flow. It may also be noted that the valves in FIGS. 14 and 16, when the vanes are in the open position, offer better passage to the flow than the valves in FIGS. 15 and 17. The segments of the tube 9, 10 may be provided with connecting elements 12, 13 at their ends.

The valves described above feature numerous advantages. In the first instance, they are of simple and rapid manufacture, since the valve as a whole can be manufactured from one piece in the course of an injection moulding operation. The moulds can be prepared with all the precision required for the purpose of the active surfaces of the different elements to play their part. In particular, the sections of the valves can be designed in the form of complementary surfaces, which, in the natural closed position, support each other in such a way that opening takes place spontaneously as soon as the air flow is directed in the desired direction (arrow in FIG. 9).

The design does not feature any obstacle at all to the passage of the air in the open position, or change its direction, or its characteristics.

Accordingly, it can be seen that the symmetry of the shapes and the aerodynamic characteristics ensure that the vanes open completely and that they close immediately, solely as a function of the direction of movement of the air flow.

The risk of the deposition of particles on the various parts inducing any shocks is thereby avoided, and the outer layers are not disturbed; the flow remains laminar, which is particularly important when used in respiration support equipment for the use by patients suffering from asthma, for example.

The same advantages may also justify the use of the valves described in other medical sectors, such as cardiology, or in general terms in the conducting and distribution of gases, liquids, powders, grains, etc. on an industrial scale.

I claim:

1. A valve for medical and therapeutic use comprising a fitting in the form of a rigid frame and a shutoff device consisting of an assembly of vanes, with surfaces which are approximately flat, connected to the frame by articulations and pivoting about these articulations during the opening process under the effect of the introduction of the fluid, the frame and the vanes forming one single piece, in which the vanes are elements which are inherently rigid and the articulations are areas which are elastically deformable, being flexible about a rectilinear axis located between the vane and a corresponding portion of the frame, wherein the vanes are shaped in such a way as to ensure the maximum cross-section for the passage of the laminar airflow in the open position the retention of the fluid in the closed position by the exclusive support of their border edges against one another.

2. A valve according to claim 1, wherein the frame and the assembly of vanes are formed of the same piece in a homogenous material, the articulations being thin areas of the said piece, each located between a vane and a corresponding portion of the frame.

3. A valve according to claim 2, wherein the said homogenous material is a crystalline plastic material, polyacetal in particular.

4. A valve according to claim 1, wherein the articulations are created with the aid of an elastic material, and an elastomer in particular.

5. A valve according to claim 1, wherein the frame is circular in shape.

6. A valve according to claim 1, wherein the frame is polygonal in shape.

7. A valve according to claim 1, wherein the vanes are triangular in shape.

8. A valve according to claim 1, wherein the edges of the vanes are curved inwards in such a way as to provide a helicoidal thrust to the flow when in the open position.

9. A valve according to claim 1, wherein the frame forms one piece with a segment of the tube guiding the flow.

10. A valve according to claim 9, wherein the segment of tube features recesses intended to accommodate the vanes in the open position.

11. A valve according to claim 1, wherein the frame is incorporated with a segment of the tube guiding the flow.

12. A valve according to claim 11, wherein the segment of tube features recesses intended to accommodate the vanes in the open position.

13. The use of a valve according to claim 1 in medical equipment, and particular in respiratory equipment.

* * * * *

UNITED STATES PATENT AND TRADEMARK OFFICE
CERTIFICATE OF CORRECTION

PATENT NO. : 6,035,896
DATED : March 14, 2000
INVENTOR(S) : Claude Liardet

It is certified that error appears in the above-indentified patent and that said Letters Patent is hereby corrected as shown below:

In column 4, line 34, please delete "the," second occurrence.

In column 5, line 20, please insert --and-- after "position," first occurrrence.

Signed and Sealed this

Tenth Day of April, 2001

*Attest:*

NICHOLAS P. GODICI

*Attesting Officer*    *Acting Director of the United States Patent and Trademark Office*